United States Patent
Zhang et al.

(10) Patent No.: US 7,236,290 B1
(45) Date of Patent: Jun. 26, 2007

(54) ELECTROPHORETIC MEDIUM WITH IMPROVED STABILITY

(75) Inventors: Libing Zhang, Sharon, MA (US); Charles H. Honeyman, Allston, MA (US)

(73) Assignee: E Ink Corporation, Cambridge, MA (US)

(*) Notice: Subject to any disclaimer, the term of this patent is extended or adjusted under 35 U.S.C. 154(b) by 1432 days.

(21) Appl. No.: 09/624,898

(22) Filed: Jul. 25, 2000

(51) Int. Cl.
G02B 26/00 (2006.01)
B01D 57/02 (2006.01)
G09G 3/34 (2006.01)

(52) U.S. Cl. .................. 359/296; 359/452; 204/450; 345/107

(58) Field of Classification Search ............ 345/107, 345/105, 108; 204/450, 600, 606; 359/452, 359/253, 296
See application file for complete search history.

(56) References Cited

U.S. PATENT DOCUMENTS

| | | | |
|---|---|---|---|
| 2,800,457 A | 7/1957 | Green et al. ............ 252/316 |
| 3,384,488 A | 5/1968 | Tulagin et al. ............ 96/88 |
| 3,585,381 A | 6/1971 | Hodson et al. ............ 250/47 |
| 3,612,758 A | 10/1971 | Evans et al. ............ 178/5.4 R |
| 3,668,106 A | 6/1972 | Ota ............ 204/299 |
| 3,756,693 A | 9/1973 | Ota ............ 345/107 |
| 3,767,392 A | 10/1973 | Ota ............ 96/1 |
| 3,772,013 A | 11/1973 | Wells ............ 96/1.3 |
| 3,792,308 A | 2/1974 | Ota ............ 315/150 |
| 3,850,627 A | 11/1974 | Wells et al. ............ 96/1.3 |
| 3,870,517 A | 3/1975 | Ota et al. ............ 96/1.5 |
| 4,001,140 A | 1/1977 | Foris et al. ............ 252/316 |
| 4,043,654 A | 8/1977 | Silverberg ............ 355/3 P |
| 4,068,927 A | 1/1978 | White ............ 359/296 |
| 4,071,430 A | 1/1978 | Liebert ............ 204/299 R |
| 4,093,534 A | 6/1978 | Carter et al. ............ 359/296 |
| 4,113,362 A | 9/1978 | Saxe et al. ............ 359/296 |

(Continued)

FOREIGN PATENT DOCUMENTS

| | | |
|---|---|---|
| GB | 1465701 | 3/1977 |
| JP | 51-130241 A | 11/1976 |
| JP | 55-096922 A | 7/1980 |
| JP | 55-105227 A | 8/1980 |
| JP | 59-165028 A | 9/1984 |

(Continued)

OTHER PUBLICATIONS

Beilin, S., et al, "8.5: 2000–Character Electrophoretic Display", SID 86 Digest, 136 (1986).

Blazo, S.F., "High Resolution Electrophoretic Display with Photoconductor Addressing",SID Digest 1982, p. 152.

Chiang, A., "Conduction Mechanism of Charge Control Agents Used in Electrophoretic Display Devices", Proceeding of the S.I.D., 18, 275 (1977).

Chiang, A., et al., "A High Speed Electrophoretic Matrix Display", SID 80 Digest (1980), 114.

(Continued)

*Primary Examiner*—Georgia Epps
*Assistant Examiner*—Timothy J Thompson
(74) *Attorney, Agent, or Firm*—David J. Cole

(57) ABSTRACT

An electrophoretic medium comprises a liquid and at least one particle disposed within the liquid and capable of moving therethrough on application of an electric field to the medium. The medium further comprises a free radical scavenger selected from the group consisting of (a) stable free radicals; and (b) polymeric free radical scavengers comprising a plurality of free radical scavenging groups attached to a polymeric chain. The medium is desirably encapsulated.

23 Claims, 3 Drawing Sheets

U.S. PATENT DOCUMENTS

| | | | |
|---|---|---|---|
| 4,123,346 A | 10/1978 | Ploix | 204/299 R |
| 4,126,528 A | 11/1978 | Chiang | 204/180 |
| 4,126,854 A | 11/1978 | Sheridon | 340/373 |
| 4,164,365 A | 8/1979 | Saxe | 359/296 |
| 4,203,106 A | 5/1980 | Dalisa et al. | 340/787 |
| 4,218,302 A | 8/1980 | Dalisa et al. | 204/299 R |
| 4,247,175 A | 1/1981 | Saxe | 359/296 |
| 4,272,596 A | 6/1981 | Harbour et al. | 430/37 |
| 4,273,672 A | 6/1981 | Vassiliades | 252/316 |
| 4,285,801 A | 8/1981 | Chiang | 204/299 R |
| 4,298,448 A | 11/1981 | Muller et al. | 204/299 R |
| 4,305,807 A | 12/1981 | Somlyody | 204/299 R |
| 4,311,361 A | 1/1982 | Somlyody | 359/296 |
| 4,314,013 A | 2/1982 | Chang | 430/37 |
| 4,407,565 A | 10/1983 | Saxe | 359/296 |
| 4,418,346 A | 11/1983 | Batchelder | 340/787 |
| 4,450,440 A | 5/1984 | White | 340/753 |
| 4,522,472 A | 6/1985 | Liebert et al. | 359/296 |
| 4,598,960 A | 7/1986 | DiSanto et al. | 339/17 M |
| 4,620,916 A | 11/1986 | Zwemer et al. | 204/299 |
| 4,643,528 A | 2/1987 | Bell, Jr. | 349/166 |
| 4,648,956 A | 3/1987 | Marshall et al. | 204/299 EC |
| 4,655,897 A | 4/1987 | DiSanto et al. | 204/299 R |
| 4,680,103 A | 7/1987 | Beilin et al. | 204/299 R |
| 4,690,749 A | 9/1987 | Van Alstine et al. | 204/299 R |
| 4,696,961 A | 9/1987 | Cantatore | 524/100 |
| 4,742,345 A | 5/1988 | DiSanto et al. | 340/787 |
| 4,746,917 A | 5/1988 | DiSanto et al. | 340/787 |
| 4,762,872 A | 8/1988 | Lai et al. | 524/100 |
| 4,769,443 A | 9/1988 | Cantatore | 528/423 |
| 4,833,464 A | 5/1989 | DiSanto et al. | 340/793 |
| 4,846,893 A | 7/1989 | Akasaki et al. | 106/500 |
| 4,889,603 A | 12/1989 | DiSanto et al. | 204/180.1 |
| 4,891,245 A | 1/1990 | Micale | 427/213.3 |
| 4,947,157 A | 8/1990 | DiSanto et al. | 340/787 |
| 4,947,159 A | 8/1990 | DiSanto et al. | 340/787 |
| 5,006,212 A | 4/1991 | DiSanto et al. | 204/192.14 |
| 5,017,225 A | 5/1991 | Nakanishi et al. | 106/21 |
| 5,041,824 A | 8/1991 | DiSanto et al. | 340/787 |
| 5,066,559 A | 11/1991 | Elmasry et al. | 430/111 |
| 5,066,946 A | 11/1991 | DiSanto et al. | 340/787 |
| 5,098,477 A | 3/1992 | Vieira et al. | 106/22 |
| 5,174,882 A | 12/1992 | DiSanto et al. | 204/299 R |
| 5,187,609 A | 2/1993 | DiSanto et al. | 359/296 |
| 5,216,416 A | 6/1993 | DiSanto et al. | 340/787 |
| 5,223,115 A | 6/1993 | DiSanto et al. | 204/299 R |
| 5,223,823 A | 6/1993 | DiSanto et al. | 340/787 |
| 5,247,290 A | 9/1993 | DiSanto et al. | 345/107 |
| 5,250,938 A | 10/1993 | DiSanto et al. | 345/107 |
| 5,254,981 A | 10/1993 | DiSanto et al. | 345/107 |
| 5,266,937 A | 11/1993 | DiSanto et al. | 345/107 |
| 5,276,438 A | 1/1994 | DiSanto et al. | 345/107 |
| 5,279,511 A | 1/1994 | DiSanto et al. | 445/24 |
| 5,279,773 A | 1/1994 | Saxe | 252/585 |
| 5,293,528 A | 3/1994 | DiSanto et al. | 345/107 |
| 5,298,833 A | 3/1994 | Hou | 313/483 |
| 5,302,235 A | 4/1994 | DiSanto et al. | 156/643 |
| 5,304,439 A | 4/1994 | DiSanto et al. | 430/20 |
| 5,315,312 A | 5/1994 | DiSanto et al. | 345/107 |
| 5,345,251 A | 9/1994 | DiSanto et al. | 345/107 |
| 5,359,346 A | 10/1994 | DiSanto et al. | 345/107 |
| 5,380,362 A | 1/1995 | Schubert | 106/493 |
| 5,402,145 A | 3/1995 | DiSanto et al. | 345/107 |
| 5,403,518 A | 4/1995 | Schubert | 252/572 |
| 5,411,656 A | 5/1995 | Schubert | 204/299 R |
| 5,412,398 A | 5/1995 | DiSanto et al. | 345/107 |
| 5,460,688 A | 10/1995 | DiSanto et al. | 216/5 |
| 5,467,107 A | 11/1995 | DiSanto et al. | 345/107 |
| 5,467,217 A | 11/1995 | Check, III | 359/296 |
| 5,496,875 A | 3/1996 | Borzatta et al. | 524/99 |
| 5,498,674 A | 3/1996 | Hou et al. | 525/369 |
| 5,499,038 A | 3/1996 | DiSanto et al. | 345/107 |
| 5,561,443 A | 10/1996 | DiSanto et al. | 345/107 |
| 5,573,711 A | 11/1996 | Hou et al. | 252/572 |
| 5,583,169 A | 12/1996 | Wrobleski et al. | 524/99 |
| 5,604,070 A | 2/1997 | Rao et al. | 430/110 |
| 5,627,561 A | 5/1997 | Laspina et al. | 345/107 |
| 5,643,673 A | 7/1997 | Hou | 428/402.24 |
| 5,663,224 A | 9/1997 | Emmons et al. | 524/188 |
| 5,686,633 A | 11/1997 | Vieira et al. | 549/434 |
| 5,707,738 A | 1/1998 | Hou | 428/402 |
| 5,745,094 A | 4/1998 | Gordon, II et al. | 345/107 |
| 5,754,332 A | 5/1998 | Crowley | 359/296 |
| 5,783,614 A | 7/1998 | Chen et al. | 523/205 |
| 5,914,806 A | 6/1999 | Gordon, II et al. | 359/296 |
| 5,930,026 A | 7/1999 | Jacobson et al. | 359/256 |
| 5,932,633 A | 8/1999 | Chen et al. | 523/205 |
| 5,961,804 A | 10/1999 | Jacobson et al. | 204/606 |
| 5,964,935 A | 10/1999 | Chen et al. | 106/401 |
| 6,014,247 A | 1/2000 | Winter et al. | 359/296 |
| 6,017,584 A | 1/2000 | Albert et al. | 427/313.3 |
| 6,025,896 A | 2/2000 | Hattori et al. | 349/86 |
| 6,067,185 A | 5/2000 | Albert et al. | 359/296 |
| 6,113,810 A | 9/2000 | Hou et al. | 252/572 |
| 6,117,368 A | 9/2000 | Hou | 252/572 |
| 6,118,426 A | 9/2000 | Albert et al. | 345/107 |
| 6,120,588 A | 9/2000 | Jacobson | 106/31.16 |
| 6,120,839 A | 9/2000 | Comiskey et al. | 427/213.3 |
| 6,124,851 A | 9/2000 | Jacobson | 345/206 |
| 6,130,773 A | 10/2000 | Jacobson et al. | 359/296 |
| 6,130,774 A | 10/2000 | Albert et al. | 359/296 |
| 6,172,798 B1 | 1/2001 | Albert et al. | 359/296 |
| 6,172,878 B1 | 1/2001 | Takabayashi et al. | 361/760 |
| 6,177,921 B1 | 1/2001 | Comiskey et al. | 345/107 |
| 6,225,971 B1 * | 5/2001 | Gordon, II et al. | 345/107 |
| 6,262,833 B1 * | 7/2001 | Loxley et al. | 359/296 |

FOREIGN PATENT DOCUMENTS

| | | |
|---|---|---|
| JP | 60-189731 A | 9/1985 |
| JP | 62-183439 A | 8/1987 |
| JP | 62-231930 A | 10/1987 |
| JP | 62-269124 A | 11/1987 |
| JP | 01-086116 A | 3/1989 |
| JP | 01-267525 A | 10/1989 |
| JP | 10-248182 A | 10/1989 |
| JP | 02-141730 A | 5/1990 |
| JP | 02-189525 A | 7/1990 |
| JP | 02-223932 A | 9/1990 |
| JP | 02-223933 A | 9/1990 |
| JP | 02-284123 A | 11/1990 |
| JP | 05-061421 A | 3/1993 |
| JP | 05-173193 A | 7/1993 |
| JP | 05-307197 A | 11/1993 |
| JP | 09-031453 A | 2/1997 |
| JP | 10-149118 A | 6/1998 |
| JP | 11-202804 A | 7/1999 |
| JP | 11-212499 A | 8/1999 |
| JP | 11-219135 A | 8/1999 |
| WO | WO 98/41898 | 9/1988 |
| WO | WO 92/15982 | 9/1992 |
| WO | WO 93/02443 | 2/1993 |
| WO | WO 94/24236 | 10/1994 |
| WO | WO 95/05622 | 2/1995 |
| WO | WO 95/06307 | 3/1995 |
| WO | WO 95/07527 | 3/1995 |
| WO | WO 95/10107 | 4/1995 |
| WO | WO 95/33085 | 12/1995 |
| WO | WO 97/04398 | 2/1997 |
| WO | WO 98/03896 | 1/1998 |
| WO | WO 98/19208 | 5/1998 |
| WO | WO 98/41899 | 9/1998 |

| WO | WO 99/10767 | 3/1999 |
| WO | WO 99/10768 | 3/1999 |
| WO | WO 99/10769 | 3/1999 |
| WO | WO 99/47970 | 9/1999 |
| WO | WO 99/53371 | 10/1999 |
| WO | WO 99/53373 | 10/1999 |
| WO | WO 99/56171 | 11/1999 |
| WO | WO 99/59101 | 11/1999 |
| WO | WO 99/60554 | 11/1999 |
| WO | WO 99/67678 | 12/1999 |
| WO | WO 00/03291 | 1/2000 |
| WO | WO 00/03349 | 1/2000 |
| WO | WO 00/05313 | 2/2000 |
| WO | WO 00/05704 | 2/2000 |
| WO | WO 00/20921 | 4/2000 |
| WO | WO 00/20922 | 4/2000 |
| WO | WO 00/20923 | 4/2000 |
| WO | WO 00/26761 | 5/2000 |
| WO | WO 00/36465 | 6/2000 |
| WO | WO 00/36560 | 6/2000 |
| WO | WO 00/36666 | 6/2000 |
| WO | WO 00/38000 | 6/2000 |
| WO | WO 00/38001 | 6/2000 |

OTHER PUBLICATIONS

Comiskey, B., et al., "An electrophoretic ink for all-printed reflective electronic displays", Nature, 394, 253 (1998).

Comiskey, B., et al., "Electrophoretic Ink: A Printable Display Material", SID 97 Digest (1997), p. 75.

Croucher, M.D., et al., "Electrophoretic Display: Materials as Related to Performance", Photog. Sci. Eng., 25, 80 (1981).

Dalisa, A.L., "Electrophoretic Display Technology", IEEE Trans. Electron Dev., ED–24, 827 (1977).

Drzaic, P., et al., "A Printed and Rollable Bistable Electronic Display", SID 98 Digest (1998), p. 1131.

Fitzhenry, B., "Identification of a Charging Mechanism using Infrared Spectroscopy", Appl. Spectroscopy, 33, 107 (1979).

Fitzhenry, B., "Optical effects of adsorption of dyes on pigment used in electrophoretic image displays", Appl. Optics., 18, 3332 (1979).

Fitzhenry–Ritz, B., "Optical Properties of Electrophoretic Image Displays", Proceedings of the S.I.D., 22, 300 (1981).

Gutcho, M.H., Microcapsules and MIcroencapsulation Techniques, Noyes Data Corp., Park Ridge NJ, (1976), p. 65–130, 178–193, 279–343.

Hopper, M.A., et al., "An Electrophoretic Display, Its Properties, Model and Addressing", IEEE Trans. Electron Dev., ED–26, 1148 (1979).

Kornfeld, A Defect–Tolerant Active–Matrix Electrophoretic Display, SID Digest, 1984, p. 142.

Lewis et al., "Gravitational, Inter–Particle and Particle–Electrode Forces in the Electrophoretic Display", Proceedings of the SID, 18, 235 (1977).

Lewis, J.C., et al., "Electrophoretic Displays", in Kmetz, A. R., et al., "Nonemissive Electrooptic Displays", Plenum Press, New York (1975).

Murau, P., "Characteristics of an X–Y Addressed Electrophoretic Image Display (EPID)," SID 84 Digest (1984) p. 141.

Murau, P., et al., "The understanding and elimination of some suspension instabilities in an electrophoretic display", J. Appl. Phys., 49, 4820 (1978).

Nakamura, E., et al., "Development of Electrophoretic Display Using Microcapsulated Suspension," SID 98 Digest (1998), p. 1014.

Ota, I., et al., "Developments in Electrophoretic Displays", Proceedings of the SID, 18, 243 (1977).

Ota, I., et al., "Electrophoretic display devices", Laser 75 Optoelectronics Conference Proceedings, 145 (1975).

Ota, I., et al., "Electrophoretic Image Display (EPID) Panel", Proceedings of the IEEE, 61, 832 (1973).

Shiffman, R R., et al., "An Electrophoretic Image Display with Internal NMOS Address Logic and Display Drivers," Proceedings of the SID, 1984, vol. 25, 105 (1984).

Singer, B., et al., "An X–Y Addressable Electrophoretic Display," Proceedings of the SID, 18, 255 (1977).

Vance, D.W., "Optical Characteristics of Electrophoretic Displays", Proceedings of the SID, 18, 267 (1977).

Vandegaer, J.E. (ed.), "Microencapsulation Processes and Applications", pp. v–x, 1–180 (Plenum Press, New York 1974).

White, R., "An Electrophoretic Bar Graph Display," Proceedings of the SID, 22, 173 (1981).

* cited by examiner

ELECTROPHORETIC MEDIUM WITH IMPROVED STABILITY

BACKGROUND OF THE INVENTION

This invention relates to an electrophoretic medium with improved stability. More specifically, it relates to an electrophoretic medium which contains a stable free radical or polymeric radical scavenger to improve the stability of the medium. The electrophoretic medium also desirably contains an ultra-violet absorber and/or quencher.

Electrophoretic displays have been the subject of intense research and development for a number of years. Such displays can have attributes of good brightness and contrast, wide viewing angles, state bistability, and low power consumption when compared with liquid crystal displays. (The terms "bistable" and "bistability" are used herein in their conventional meaning in the art to refer to displays comprising display elements having first and second display states differing in at least one optical property, and such that after any given element has been driven, by means of an addressing pulse of finite duration, to assume either its first or second display state, after the addressing pulse has terminated, that state will persist for at least several times, for example at least four times, the minimum duration of the addressing pulse required to change the state of the display element.) Nevertheless, problems with the long-term image quality of these displays have prevented their widespread usage. For example, particles that make up electrophoretic displays tend to cluster and settle, resulting in inadequate service-life for these displays.

An encapsulated, electrophoretic display typically does not suffer to the same degree from the clustering and settling failure mode of traditional electrophoretic devices and provides further advantages, such as the ability to print or coat the display on a wide variety of flexible and rigid substrates. (Use of the word "printing" is intended to include all forms of printing and coating, including, but without limitation: pre-metered coatings such as patch die coating, slot or extrusion coating, slide or cascade coating, curtain coating; roll coating such as knife over roll coating, forward and reverse roll coating; gravure coating; dip coating; spray coating; meniscus coating; spin coating; brush coating; air knife coating; silk screen printing processes; electrostatic printing processes; thermal printing processes; ink jet printing processes; and other similar techniques.) Thus, the resulting display can be flexible. Further, because the display medium can be printed (using a variety of methods), the display itself can be made inexpensively.

However, even encapsulated prior art electrophoretic displays have working lifetimes less than is entirely desirable for commercial purposes. Depending upon operational parameters, such as the voltage applied to the electrophoretic medium and the frequency at which any given pixel of the display is switched, and environmental parameters, such as the temperature, humidity and light intensity under which the electrophoretic display is operated, various components of the electrophoretic medium may be subject to electrochemical and/or photochemical reactions, which may cause problems such as aggregation of the electrophoretic particles or discoloration of a dye present in the liquid suspension medium.

Previous attempts have been made to solve these problems in unencapsulated displays. For example, U.S. Pat. No. 4,620,916 (Zwemer et al.) notes that "there have been problems in realizing commercially successful display devices based upon electrophoretic principles. Among the problems have been the difficulty of achieving sufficient stability in the electrophoretic cell so as to sustain an acceptable number of switching operations. Chemical reactions in the suspension of the cell adversely affect operating lifetime and the known electrophoretic display devices have generally had a limited useful life." In an attempt to solve such problems Zwemer teaches that there should be added to the working liquid of the electrophoretic display a "degradation retardant [which] consists essentially of a redox agent, a redox agent precursor, an inhibitor agent or mixtures thereof. The redox agent is capable of being reversibly oxidized and reduced during operation of the electrophoretic display device. The redox agent precursor is capable of reacting with free radical species of the working liquid to form the redox agent as a reaction product. The inhibitor agent is capable of reacting with free radical species to terminate chemical chain reactions during operation of the electrophoretic display device."

Although the degradation retardants disclosed in Zwemer do relieve some of the problems discussed above, these retardants are not entirely satisfactory. In particular, the specific degradation retardants disclosed in Zwemer do not absorb ultra-violet light and are not effective in preventing light-induced degradation of an electrophoretic medium. Also, the Zwemer retardants cause problems in encapsulated electrophoretic media since under high humidity conditions they may diffuse through the capsule wall into the binder which is normally used in an encapsulated electrophoretic medium to bind the capsules to one another and cause degradation (browning) of this binder or discoloration of the electrodes of the electrophoretic display.

It has now been found that the problems discussed above can be reduced, and the working lifetime of electrophoretic media and of displays incorporating such media increased, by adding to the electrophoretic medium either a stable free radical or a polymeric free radical scavenger.

SUMMARY OF THE INVENTION

Accordingly, this invention provides an electrophoretic medium comprising a liquid and at least one particle disposed within the liquid and capable of moving therethrough on application of an electric field to the medium. The electrophoretic medium further comprises a free radical scavenger selected from the group consisting of (a) stable free radicals; and (b) polymeric free radical scavengers comprising a plurality of free radical scavenging groups attached to a polymeric chain.

This invention also provides an electrophoretic display comprising an electrophoretic medium of the present invention in combination with first and second electrodes disposed on opposed sides of the electrophoretic medium, at least one of the first and second electrodes being light transmissive.

DETAILED DESCRIPTION OF THE INVENTION

Figure 1:
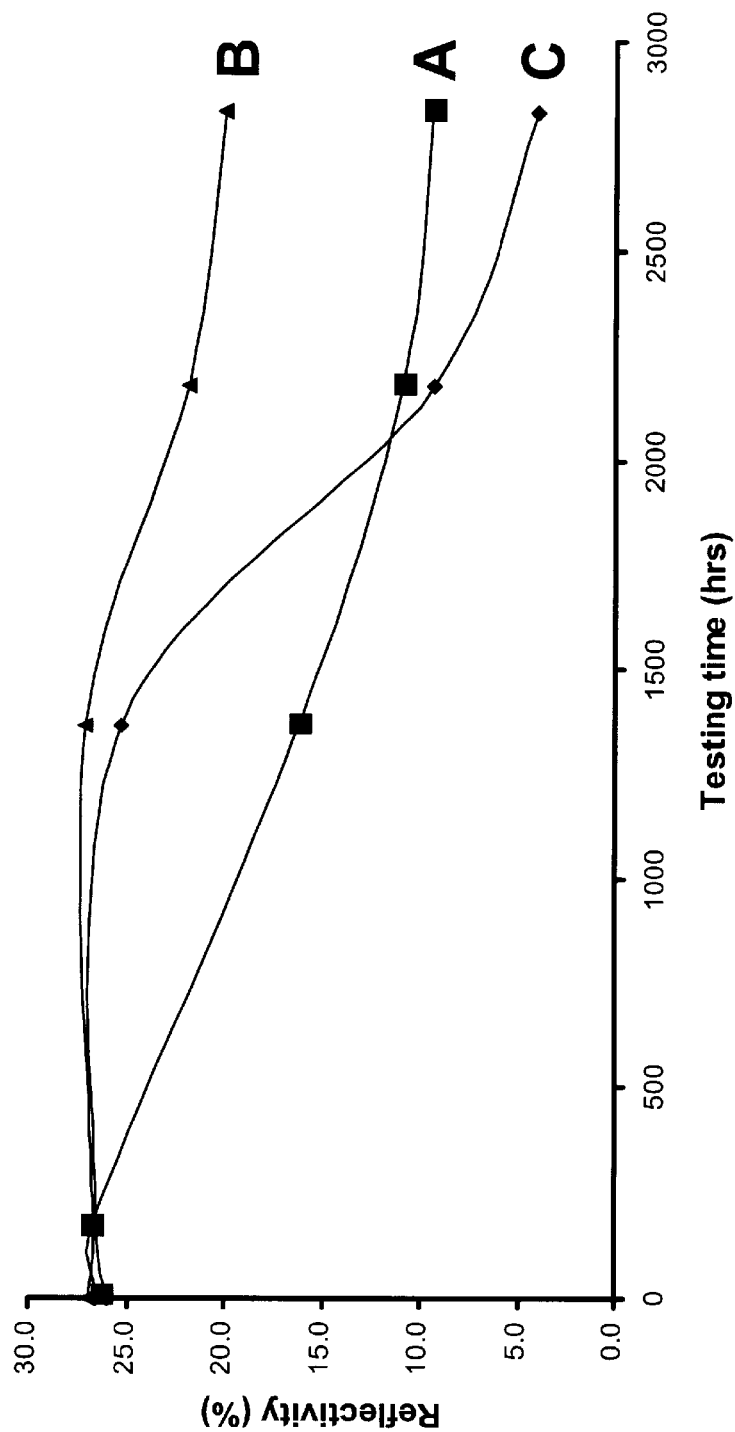
FIGS. 1, 2 and 3 of the accompanying drawings show graphically the variation with operating time of the reflectivities of the white state of certain preferred displays of the present invention, as described in Examples 1, 2 and 3 respectively.

As already mentioned, the present invention improves the working lifetime of an electrophoretic medium by adding to the medium either a stable free radical or a polymeric free radical scavenger. Since the characteristics of these two groups of compounds differ considerably, the two groups will first be discussed separately.

Stable free radicals are compounds which exist naturally in free radical form, as shown, for example, by their paramagnetism. Such stable free radicals are available commercially and have previously been used to improve the weathering properties of polymers. The preferred group of stable free radicals for use in the present media are such radicals derived from an amine oxide, such as a piperidine oxide, especially a 2,2,6,6-tetraalkylpiperidine oxide. The presently preferred specific stable free radical is 2,2,6,6-tetramethylpiperidyloxy; this material, which is of the formula:

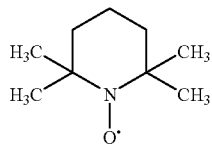

is available commercially from Sigma-Aldrich, Inc., P.O. Box 2060, Milwaukee Wis. 53201 under the tradename TEMPO, by which name it may called hereinafter.

This compound has a number of properties which render it especially suitable for use in electrophoretic media. As will appear from the detailed discussion below regarding the preferred materials for use in electrophoretic media, such media typically use a hydrocarbon liquid as the suspension fluid, since hydrocarbons normally have higher electrical resistivities than aqueous liquids, thus reducing the current which is needed to drive the display containing the electrophoretic medium. Encapsulated electrophoretic media typically have capsule walls formed from an aqueous medium so that little or no mixing of the capsule wall phase and the internal phase occurs during formation of the capsules, which usually involves first forming a complex droplet of the internal phase surrounded by a liquid capsule wall phase, and then solidifying the latter phase to form the final capsule wall. For example, one presently preferred electrophoretic medium has an internal phase comprising titania particles suspended in a dyed hydrocarbon and a capsule wall formed from a gelatin/acacia complex. TEMPO has significant solubility (>0.5 g/L) in hydrocarbons, but is essentially insoluble in water. Accordingly, TEMPO can be dissolved in the hydrocarbon liquid of the internal phase of this preferred electrophoretic medium in amounts sufficient to provide its desired degradation-retarding function, but shows little or no tendency to migrate into the capsule wall or the binder surrounding the capsules. Its has also been found empirically that TEMPO does not substantially affect the resistivity of the internal phase, the electrophoretic mobility of the titania particles or the electro-optic properties of the electrophoretic medium. Furthermore, TEMPO does not significantly affect the encapsulation process used to form the capsules, presumably because this compound does not significantly affect the interfacial tension between the hydrocarbon and aqueous phases used in this process.

It is believed (although this invention is in no way limited by this belief) that one reason why stable free radicals are more effective in extending the working lifetime of electrophoretic media than the non-radical scavengers (i.e., free radical scavengers which are not themselves stable free radicals) described in Zwemer is that the reaction between a non-radical scavenger and a free radical (generated, for example, by a photoinitiated reaction at the surface of the titania particles) inevitably leads to the formation of a second free radical, which may itself have undesirable effects upon the electrophoretic medium. The free radicals are only eliminated by the combination of two free radicals to produce a non-radical species, and this is a relatively slow process. In contrast, a stable free radical can immediately combine with a photogenerated free radical to form a non-radical species, thus reducing the concentration of free radical present in the electrophoretic medium and minimizing the deleterious effects of such radicals upon the medium.

The polymeric free radical scavengers used in the electrophoretic medium of the present invention comprise a plurality of free radical scavenging groups attached to a polymeric chain or "backbone", which may, for example, be a polymethylene chain. The radical scavenging groups may be, for example, nitrogenous heterocyclic groups, preferably piperidine groups. An especially preferred class of radical scavenging groups are 2,2,6,6-substituted piperidine groups bearing a hydrocarbon or hydrocarbonoxy group on the nitrogen atom, such groups preferably being attached to the polymeric chain at their 4-position. Such materials are available commercially, being sold, for example, under the trade names Uvinul 5050H (from BASF Corporation, 3000 Continental Drive North, Mount Olive, N.J. 07828—"Uvinul" is a Registered Trade Mark; this material is an oligomer with a molecular weight of about 3,500) and Ferro UV-check AM 806 (from Ferro Corporation, 1000 Lakeside Avenue, Cleveland, Ohio 44114; this material is an oligomer with a molecular weight in excess of 2,400).

It is believed (although the invention is in no way limited by this belief) that one reason why polymeric free radical scavengers are more effective than the low molecular weight scavengers described in Zwemer is that the polymeric scavengers show less tendency to diffuse out of the electrophoretic medium into the capsule wall and/or binder of an encapsulated electrophoretic medium. This reduced diffusion of polymeric scavengers not only reduces potentially undesirable reactions between the scavenger and the capsule wall or binder, but also ensures that the polymeric scavengers remain within the electrophoretic medium where they can exert their desired radical-removing effects.

The optimum amount of any specific free radical scavenger for use in any specific electrophoretic medium may readily be determined empirically using lifetime tests such as those described in the Examples below. As will be seen from these Examples, and as is well known to those skilled in the art of preparing electrophoretic displays, degradation reactions in such displays manifest themselves as a gradual reduction in the difference between the two display states of the display. In the case of a typical display in which one display state is black or dark and the other is white or light, the degradation reactions result in a gradual decrease in the reflectivity of the light or white state and a gradual increase in the reflectivity of the black or dark state, these changes being readily measurable by an optical densitometer. Addition of a free radical scavenger in accordance with the present invention increases the operating lifetime of the display, this operating lifetime being the period for which an electrophoretic display can withstand illumination before a predetermined decrease in the reflectivity of the light state occurs (the changes in reflectivity of the light state are greater than the corresponding change in the dark state and hence can normally be measured more accurately). As the concentration of the free radical scavenger is gradually increased, it will be found that this time increases, but eventually a point is reached at which addition of further scavenger brings about no further increase in this time. In general, it is found that the optimum concentration of free radical scavenger will lie in the range of from about 0.01 to 1 percent by weight of the electrophoretic medium, and most commonly from about 0.05 to about 0.2 percent by weight.

In addition to the free radical scavenger, at least in some cases it is advantageous for the electrophoretic medium to contain an ultra-violet absorber and/or quencher; the inclusion of such an absorber and/or quencher may further increase the resistance of the electrophoretic medium to the undesirable degradation reactions previously discussed, especially when the medium is exposed to intense illumination. A wide variety of ultra-violet absorbers and quenchers may be used, for example triazine derivatives, benzoxazinones, hydroxy-substituted benzophenones, hydroxy-substituted benzotriazoles, nickel complexes, formamidines and oxamide derivatives. Examples of suitable ultra-violet absorbers and quenchers available commercially are:

Triazines:
  Uvinul T-150 (BASF Corporation)
  Tinuvin (Registered Trade Mark) 400, 1577FF, 1545 (Ciba Specialty Chemicals, 560 White Plains Road, Tarrytown N.Y. 10591)
  Cyasorb (Registered Trade Mark) 1164, Cyagard (Registered Trade Mark) 1164L (Cytec Technology Corp., 1105 North Market Street Wilmington Del. 19801)
Benzoxazinones:
  Cyagard 3638 (Cytec Technology Corp.)
Hydroxy-substituted benzophenones:
  Uvinul 400, 3048, D49, D50 (BASF Corporation)
  MaxGard (Registered Trade Mark) 200, 800 (Garrison Industries, Inc., 135 Louis Hurley Road, El Dorado Ak. 71731)
  Mark 1535 (Witco Corporation, One American Lane, Greenwich Conn. 06831)
  Cyasorb 284, 2098, 2126, UV 24, Cyagard UV 9, UV 531 (Cytec Technology Corp.)
Hydroxy-substituted benzotriazoles:
  Tinuvin P, 99, 109, 320, 326, 327, 328, 384, 571, 840, 900, 928, 1130 (Ciba Specialty Chemicals)
  Cyagard UV 5411 (Cytec Technology Corp.)
  Norbloc 6000, 7966 (Noramco, Inc., 500 Swedes Landing Road, Wilmington, Del. 19801-4417)
Nickel complexes:
  Cyasorb 1084 (Cytec Technology Corp.)
Esters:
  Seesorb 201 (Sun Chemical Corporation, 222 Bridge Plaza South, Fort Lee, N.J. 07024—phenyl salicylate)
  Uvinul 3035, P25 (BASF Corporation)
  Cyasorb UV 1988 (Cytec Technology Corp.—benzylidene malonate ester)
  Tinuvin 120 (Ciba Specialty Chemicals) and Cyasorb UV 2908 (Cytec Technology Corp.) (both hindered benzoates)
  Eastman Inhibitor RMB (Eastman Chemical Company, 100 North Eastman Road, P. O. Box 511, Kingsport Tenn. 37662-5075—hydroxyphenyl benzoate)
  Givsorb UV-13 (Givaudan Roure Flavours Corp., 1199 Edison Drive, Cincinnati Ohio 45216; "Givsorb" is a Registered Trade Mark—propenoate/cinnamate)
Formamidines:
  Givsorb UV-1 (Givaudan Roure Flavours Corp.)
  Sanduvor (Registered Trade Mark) EPU (Clariant Corporation, 4000 Monroe Road, Charlotte, N.C. 28205)
Ketones:
  Givsorb UV-15 (Givaudan Roure Flavours Corp.—aliphatic ketones)
  Givsorb UV-14 (Givaudan Roure Flavours Corp.—hydroxy-substituted aromatic propanedione)
Oxamide derivatives:
  Sanduvor VSU (Clariant Corporation—oxanilide)
Other:
  Quercetin (EM Industries, Inc., 7 Skyline Drive, Hawthorne N.Y. 10532)
  Givsorb UV-16 (Givaudan Roure Flavours Corp.—acid)

As with the free radical scavengers, the optimum amount of any specific ultra-violet absorber and/or quencher for use in any specific electrophoretic medium is best determined empirically using lifetime tests. However, in general the ultra-violet absorber and/or quencher will be used in an amount of from about 0.02 to about 5, and preferably from about 0.2 to about 2 percent by weight of the electrophoretic medium; the optimum amount of ultra-violet absorber and/or quencher will vary with a number of factors, including the ultra-violet absorption of the material used, the thickness of the electrophoretic medium and the amount and type of electrophoretic particles present in the medium.

For reasons already discussed, it is generally preferred that the electrophoretic medium of the present invention be encapsulated, that is to say that the medium comprise a plurality of capsules, each of which has a capsule wall enclosing the liquid and the particle(s). Desirably, such an encapsulated medium further comprises a binder disposed between the capsules and binding them to one another.

Although reference has been made throughout the foregoing description to capsules and a binder in a manner which suggests that the encapsulated electrophoretic medium of the present invention comprises a plurality of discrete capsules, the present medium may also have the form of a "polymer-dispersed electrophoretic display", hereafter abbreviated "PDED". Essentially, a PDED is a two-phase system having a discontinuous phase, which comprises a plurality of discrete droplets of an electrophoretic fluid (as usual, comprising a liquid and at least one particle disposed within the liquid and capable of moving therethrough on application of an electric field to the liquid), and a continuous phase of a polymeric material. The discrete droplets of electrophoretic fluid within a PDED may be referred to as capsules or microcapsules even though no discrete capsule membrane is associated with each individual droplet. Accordingly, references to "capsules" herein are to be construed as extending to PDED's, which are considered to be subsets of encapsulated electrophoretic displays.

As discussed in more detail below, in one form of the present electrophoretic medium the liquid has an optical property differing from that of the particle(s) suspended therein. Typically, the liquid and the particles differ in color; for example, one might have a liquid which is dyed blue and white particles formed from titania. In another form of the electrophoretic medium, there is disposed within the liquid at least one first particle having a first optical property and a first electrophoretic mobility and at least one second particle having a second optical property different from the first optical property and a second electrophoretic mobility different from the first electrophoretic mobility. The two types of particles may bear charges of opposite polarity.

An electrophoretic display of the present invention will typically comprise the electrophoretic medium in combination with first and second electrodes disposed on opposed sides of the electrophoretic medium, at least one of the first and second electrodes being light transmissive; the light transmissive electrode forms a viewing surface through which an observer views the medium. Such a display may comprise first and second substrates disposed on opposed sides of the electrophoretic medium, the first and second substrates being secured to the first and second electrodes respectively.

Apart from the use of the free radical scavengers, and the optional ultra-violet absorbers and/or quenchers already described, the electrophoretic displays of the present invention resemble prior art electrophoretic displays, and hence the present displays can make use of any known materials and processes for the production of such displays, as described, for example, in U.S. Pat. Nos. 6,017,584 and 6,067,185, and in copending commonly-assigned application Ser. No. 09/413,444, filed Oct. 6, 1999, and the corresponding International Application PCT/US99/23313 (Publication No. WO 00/20922); the entire disclosures of all these patents and applications are herein incorporated by reference.

The successful construction of an encapsulated electrophoretic display requires the proper interaction of several different types of materials and processes. As already mentioned, typically such an encapsulated electrophoretic display will include a polymeric binder to bind the capsules into a coherent layer and/or to act as an adhesive to adhere the capsules to a substrate. Materials such as the polymeric binder, a capsule membrane or wall, electrophoretic particles, and the suspending fluid must all be chemically compatible. The capsule membranes may engage in useful surface interactions with the electrophoretic particles, or may act as an inert physical boundary between the fluid and the binder.

In an encapsulated electrophoretic display, the binder material surrounds the capsules and separates the two electrodes. This binder material must be compatible with the capsules and electrodes and should possess properties that allow for facile printing or coating. It may also possess barrier properties for water, oxygen, ultraviolet light, the electrophoretic fluid, or other materials, Further, it may contain surfactants and cross-linking agents, which could aid in coating or durability. A polymer-dispersed electrophoretic display may be of the emulsion or phase separation type.

Desirably, the encapsulated electrophoretic medium has a plurality of non-spherical capsules disposed substantially in a single layer on a substrate. The non-spherical capsules can have a substantially planar surface on at least one side proximate a substrate. Also, the capsules can be close-packed.

Non-spherical microcapsules can be formed during the encapsulation phase by, for example, using a non-uniform shear field or a compressive pressure. Such non-spherical capsules can also be formed during the processing of the display when the binder is drying or curing. In such a system, as the binder shrinks, it pulls capsules close to one another and pulls the capsules down toward the substrate on which they have been coated. For example, an aqueous evaporative binder, such as a waterborne acrylic, urethane, or poly(vinyl alcohol), tends to exhibit such shrinking properties. Typically, a fraction of the binder, such as water, evaporates. Other evaporative binders, emulsions, or solutions also are suitable. The solvent need not be water, but can be an organic liquid or a combination of liquids.

Also, non-spherical capsules can be formed, for example, by applying a force to the film as it is drying or curing to permanently deform the capsules. Such a force can be applied by a pair of rollers, by a vacuum lamination press, by a mechanical press, or by any other suitable means. Such non-spherical capsules can also be formed by stretching the cured film in one or both of the planar axes of the film. After completion of the curing process, the capsule can protrude above the surface of the cured film, resulting in a lens effect that enhances the optical properties of the capsule. Finally, the capsule also can be formed of a material which softens in the binder, thus allowing the capsules to deform to form a flat surface when the capsules and binder are laid down and the binder is cured.

In another embodiment, a PDED is constructed in a manner similar to a polymer-dispersed liquid crystal display. A fluid is mixed with a binder. Typically, the fluid can be an oil. As the binder is dried or is cured, the fluid is pulled into non-spherical cavities. These fluid-containing cavities can be elastomeric capsules. These cavities lack discrete capsule walls.

The following Sections A–E describe useful materials for use in the various components of the electrophoretic displays of the present invention.

A. Electrophoretic Particles

There is much flexibility in the choice of particles for use in electrophoretic displays, as described above. For purposes of this invention, a particle is any component that is charged or capable of acquiring a charge (i.e., has or is capable of acquiring electrophoretic mobility), and, in some cases, this mobility may be zero or close to zero (i.e., the particles will not move). The particles may be neat pigments, dyed (laked) pigments or pigment/polymer composites, or any other component that is charged or capable of acquiring a charge. Typical considerations for the electrophoretic particle are its optical properties, electrical properties, and surface chemistry. The particles may be organic or inorganic compounds, and they may either absorb light or scatter light. The particles for use in the invention may further include scattering pigments, absorbing pigments and luminescent particles. The particles may be retroreflective, such as comer cubes, or they may be electroluminescent, such as zinc sulfide particles, which emit light when excited by an alternating electric field, or they may be photoluminescent. For example, zinc sulfide electroluminescent particles may be encapsulated with an insulative coating to reduce electrical conduction. Finally, the particles may be surface treated so as to improve charging or interaction with a charging agent, or to improve dispersability.

One particle for use in electrophoretic displays of the invention is titania. The titania particles may be coated with a metal oxide, such as aluminum oxide or silicon oxide, for example. The titania particles may have one, two, or more layers of metal-oxide coating. For example, a titania particle for use in electrophoretic displays of the invention may have a coating of aluminum oxide and a coating of silicon oxide. The coatings may be added to the particle in any order.

The electrophoretic particle is usually a pigment, a polymer, a laked pigment, or some combination of the above. A neat pigment can be any pigment, and, usually for a light colored particle, pigments such as rutile (titania), anatase (titania), barium sulfate, kaolin, or zinc oxide are useful. Some typical particles have high refractive indices, high scattering coefficients, and low absorption coefficients. Other particles are absorptive, such as carbon black or colored pigments used in paints and inks. The pigment should also be insoluble in the suspending fluid. Yellow pigments such as diarylide yellow, Hansa yellow, and benzidin yellow have also found use in similar displays. Any other reflective material can be employed for a light colored particle, including non-pigment materials, such as metallic particles.

Useful neat pigments include, but are not limited to, $PbCrO_4$, Cyan blue GT 55-3295 (American Cyanamid Company, Wayne, N.J.), Cibacron Black BG (Ciba Company, Inc., Newport, Del.), Cibacron Turquoise Blue G (Ciba), Cibalon Black BGL (Ciba), Orasol Black BRG (Ciba), Orasol Black RBL (Ciba), Acetamine Black, CBS (E. I. du Pont de Nemours and Company, Inc., Wilmington, Del., hereinafter abbreviated "du Pont"), Crocein Scarlet N Ex (du Pont) (27290), Fiber Black VF (du Pont) (30235), Luxol Fast Black L (du Pont) (Solvent Black 17), Nirosine Base No. 424 (du Pont) (50415 B), Oil Black BG (du Pont) (Solvent Black 16), Rotalin Black RM (du Pont), Sevron Brilliant Red 3 B (du Pont); Basic Black DSC (Dye Specialties, Inc.), Hectolene Black (Dye Specialties, Inc.), Azosol Brilliant Blue B (GAF, Dyestuff and Chemical Division, Wayne, N.J.) (Solvent Blue 9), Azosol Brilliant Green BA (GAF) (Solvent Green 2), Azosol Fast Brilliant Red B (GAF), Azosol Fast Orange RA Conc. (GAF) (Solvent Orange 20), Azosol Fast Yellow GRA Conc. (GAF) (13900 A), Basic Black KMPA (GAF), Benzofix Black CW-CF (GAF) (35435), Cellitazol BNFV Ex Soluble CF (GAF) (Disp. Black 9), Celliton Fast Blue AF Ex Conc (GAF) (Disp. Blue 9), Cyper Black IA (GAF) (Basic Black 3), Diamine Black CAP Ex Conc (GAF) (30235), Diamond Black EAN Hi Con. CF (GAF) (15710), Diamond Black PBBA Ex (GAF) (16505); Direct Deep Black EA Ex CF (GAF) (30235), Hansa Yellow G (GAF) (11680); Indanthrene Black BBK Powd. (GAF) (59850), Indocarbon CLGS Conc. CF (GAF) (53295), Katigen Deep Black NND Hi Conc. CF (GAF) (15711), Rapidogen Black 3 G (GAF) (Azoic Black 4); Sulphone Cyanine Black BA-CF (GAF) (26370), Zambezi Black VD Ex Conc. (GAF) (30015); Rubanox Red CP-1495 (The Sherwin-Williams Company, Cleveland, Ohio) (15630); Raven 11 (Columbian Carbon Company, Atlanta, Ga.), (carbon black aggregates with a particle size of about 25 μm), Statex B-12 (Columbian Carbon Co.) (a furnace black of 33 μm average particle size), and chrome green.

Particles may also include laked, or dyed, pigments. Laked pigments are particles that have a dye precipitated on them or which are stained. Lakes are metal salts of readily soluble anionic dyes. These are dyes of azo, triphenylmethane or anthraquinone structure containing one or more sulphonic or carboxylic acid groupings. They are usually precipitated by a calcium, barium or aluminum salt onto a substrate. Typical examples are peacock blue lake (CI Pigment Blue 24) and Persian orange (lake of CI Acid Orange 7), Black M Toner (GAF) (a mixture of carbon black and black dye precipitated on a lake).

A dark particle of the dyed type may be constructed from any light absorbing material, such as carbon black, or inorganic black materials. The dark material may also be selectively absorbing. For example, a dark green pigment may be used. Black particles may also be formed by staining latices with metal oxides, such latex copolymers consisting of any of butadiene, styrene, isoprene, methacrylic acid, methyl methacrylate, acrylonitrile, vinyl chloride, acrylic acid, sodium styrene sulfonate, vinyl acetate, chlorostyrene, dimethylaminopropylmethacrylamide, isocyanoethyl methacrylate and N-(isobutoxymethacrylamide), and optionally including conjugated diene compounds such as diacrylate, triacrylate, dimethylacrylate and trimethacrylate. Black particles may also be formed by a dispersion polymerization technique.

In the systems containing pigments and polymers, the pigments and polymers may form multiple domains within the electrophoretic particle, or be aggregates of smaller pigment/polymer combined particles. Alternatively, a central pigment core may be surrounded by a polymer shell. The pigment, polymer, or both can contain a dye. The optical purpose of the particle may be to scatter light, absorb light, or both. Useful sizes may range from 1 nm up to about 100 μm, as long as the particles are smaller than the bounding capsule. The density of the electrophoretic particle may be substantially matched to that of the suspending (i.e., electrophoretic) fluid. As defined herein, a suspending fluid has a density that is "substantially matched" to the density of the particle if the difference in their respective densities is between about zero and about two grams/milliliter ("g/ml"). This difference is preferably between about zero and about 0.5 g/ml.

Useful polymers for the particles include, but are not limited to: polystyrene, polyethylene, polypropylene, phenolic resins, du Pont Elvax resins (ethylene-vinyl acetate copolymers), polyesters, polyacrylates, polymethacrylates, ethylene acrylic acid or methacrylic acid copolymers (Nucrel Resins—du Pont, Primacor Resins—Dow Chemical), acrylic copolymers and terpolymers (Elvacite Resins—du Pont) and PMMA. Useful materials for homopolymer/pigment phase separation in high shear melt include, but are not limited to, polyethylene, polypropylene, poly(methyl methacrylate), poly(isobutyl methacrylate), polystyrene, polybutadiene, polyisoprene, polyisobutylene, poly(lauryl methacrylate), poly(stearyl methacrylate), poly(isobornyl methacrylate), poly(t-butyl methacrylate), poly(ethyl methacrylate), poly(methyl acrylate), poly(ethyl acrylate), polyacrylonitrile, and copolymers of two or more of these materials. Some useful pigment/polymer complexes that are commercially available include, but are not limited to, Process Magenta PM 1776 (Magruder Color Company, Inc., Elizabeth, N.J.), Methyl Violet PMA VM6223 (Magruder Color Company, Inc., Elizabeth, N.J.), and Naphthol FGR RF6257 (Magruder Color Company, Inc., Elizabeth, N.J.).

The pigment-polymer composite may be formed by a physical process, (e.g., attrition or ball milling), a chemical process (e.g., microencapsulation or dispersion polymerization), or any other process known in the art of particle production. For example, the processes and materials for both the fabrication of liquid toner particles and the charging of those particles may be relevant.

New and useful electrophoretic particles may still be discovered, but a number of particles already known to those skilled in the art of electrophoretic displays and liquid toners can also prove useful. In general, the polymer requirements for liquid toners and electrophoretic inks are similar, in that the pigment or dye must be easily incorporated therein, either by a physical, chemical, or physicochemical process, may aid in the colloidal stability, and may contain charging sites or may be able to incorporate materials which contain charging sites. One general requirement from the liquid toner industry that is not shared by electrophoretic inks is that the toner must be capable of "fixing" the image, i.e., heat fusing together to create a uniform film after the deposition of the toner particles.

Typical manufacturing techniques for particles may be drawn from the liquid toner and other arts and include ball milling, attrition, jet milling, etc. The process will be illustrated for the case of a pigmented polymeric particle. In such a case the pigment is compounded in the polymer, usually in some kind of high shear mechanism such as a screw extruder. The composite material is then (wet or dry) ground to a starting size of around 10 µm. It is then dispersed in a carrier liquid, for example ISOPAR® (Exxon Company, U.S.A., P.O. Box 2180, Houston Tex. 77252-2180), optionally with some charge control agent(s), and milled under high shear for several hours down to a final particle size and/or size distribution.

Another manufacturing technique for particles is to add the polymer, pigment, and suspending fluid to a media mill. The mill is started and simultaneously heated to a temperature at which the polymer swells substantially with the solvent. This temperature is typically near 100° C. In this state, the pigment is easily encapsulated into the swollen polymer. After a suitable time, typically a few hours, the mill is gradually cooled back to ambient temperature while stirring. The milling may be continued for some time to achieve a small enough particle size, typically a few microns in diameter. The charging agents may be added at this time. Optionally, more suspending fluid may be added.

Chemical processes such as dispersion polymerization, mini- or micro-emulsion polymerization, suspension polymerization precipitation, phase separation, solvent evaporation, in situ polymerization, seeded emulsion polymerization, or any process which falls under the general category of microencapsulation may be used. A typical process of this type is a phase separation process wherein a dissolved polymeric material is precipitated out of solution onto a dispersed pigment surface through solvent dilution, evaporation, or a thermal change. Other processes include chemical means for staining polymeric latices, for example with metal oxides or dyes.

B. Suspending Fluid

The suspending fluid containing the particles can be chosen based on properties such as density, refractive index, and solubility. A preferred suspending fluid has a low dielectric constant (about 2), high volume resistivity (about $10^{15}$ ohm-cm), low viscosity (less than 5 centistokes ("cst")), low toxicity and environmental impact, low water solubility (less than 10 parts per million ("ppm")), high specific gravity (greater than 1.5), a high boiling point (greater than 90° C.), and a low refractive index (less than 1.2).

The choice of suspending fluid may be based on concerns of chemical inertness, density matching to the electrophoretic particle, or chemical compatibility with both the electrophoretic particle and bounding capsule. The viscosity of the fluid should be low when movement of the particles is desired. The refractive index of the suspending fluid may also be substantially matched to that of the particles. As used herein, the refractive index of a suspending fluid "is substantially matched" to that of a particle if the difference between their respective refractive indices is between about zero and about 0.3, and is preferably between about 0.05 and about 0.2.

Additionally, the fluid may be chosen to be a poor solvent for some polymers, which is advantageous for use in the fabrication of microparticles, because it increases the range of polymeric materials useful in fabricating particles of polymers and pigments. Organic solvents, such as halogenated organic solvents, saturated linear or branched hydrocarbons, silicone oils, and low molecular weight halogen-containing polymers are some useful suspending fluids. The suspending fluid may comprise a single fluid. The fluid will, however, often be a blend of more than one fluid in order to tune its chemical and physical properties. Furthermore, the fluid may contain surface modifiers to modify the surface energy or charge of the electrophoretic particle or bounding capsule. Reactants or solvents for the microencapsulation process (oil soluble monomers, for example) can also be contained in the suspending fluid. Charge control agents can also be added to the suspending fluid.

Useful organic solvents include, but are not limited to, epoxides, such as decane epoxide and dodecane epoxide; vinyl ethers, such as cyclohexyl vinyl ether and Decave® (International Flavors & Fragrances, Inc., New York, N.Y.); and aromatic hydrocarbons, such as toluene and naphthalene. Useful halogenated organic solvents include, but are not limited to, tetrafluorodibromoethylene, tetrachloroethylene, trifluorochloroethylene, 1,2,4-trichlorobenzene and carbon tetrachloride. These materials have high densities. Useful hydrocarbons include, but are not limited to, dodecane, tetradecane, the aliphatic hydrocarbons in the Isopar® series (Exxon, Houston, Tex.), Norpar® (a series of normal paraffinic liquids), Shell-Sol® (Shell, Houston, Tex.), and Sol-Trol® (Shell), naphtha, and other petroleum solvents. These materials usually have low densities. Useful examples of silicone oils include, but are not limited to, octamethyl cyclosiloxane and higher molecular weight cyclic siloxanes, poly(methyl phenyl siloxane), hexamethyldisiloxane, and polydimethylsiloxane. These materials usually have low densities. Useful low molecular weight halogen-containing polymers include, but are not limited to, poly(chlorotrifluoroethylene) polymer (Halogenated Hydrocarbon Inc., River Edge, N.J.), Galden® (a perfluorinated ether from Ausimont, Morristown, N.J.), or Krytox® from du Pont. In a preferred embodiment, the suspending fluid is a poly (chlorotrifluoroethylene) polymer. In a particularly preferred embodiment, this polymer has a degree of polymerization from about 2 to about 10. Many of the above materials are available in a range of viscosities, densities, and boiling points.

The fluid must be capable of being formed into small droplets prior to a capsule being formed. Processes for forming small droplets include flow-through jets, membranes, nozzles, or orifices, as well as shear-based emulsifying schemes. The formation of small drops may be assisted by electrical or sonic fields. Surfactants and polymers can be used to aid in the stabilization and emulsification of the droplets in the case of an emulsion type encapsulation. One surfactant for use in displays of the invention is sodium dodecylsulfate.

It can be advantageous in some displays for the suspending fluid to contain an optically absorbing dye. This dye must be soluble in the fluid, but will generally be insoluble in the other components of the capsule. There is much flexibility in the choice of dye material. The dye can be a pure compound, or blends of dyes to achieve a particular color, including black. The dyes can be fluorescent, which would produce a display in which the fluorescence properties depend on the position of the particles. The dyes can be photoactive, changing to another color or becoming colorless upon irradiation with either visible or ultraviolet light, providing another means for obtaining an optical response. Dyes could also be polymerizable by, for example, thermal, photochemical or chemical diffusion processes, forming a solid absorbing polymer inside the bounding shell.

There are many dyes that can be used in encapsulated electrophoretic displays. Properties important here include light fastness, solubility in the suspending liquid, color, and cost. These dyes are generally chosen from the classes of azo, anthraquinone, and triphenylmethane type dyes and may be chemically modified so as to increase their solubility in the oil phase and reduce their adsorption by the particle surface.

A number of dyes already known to those skilled in the art of electrophoretic displays will prove useful. Useful azo dyes include, but are not limited to: the Oil Red dyes, and the Sudan Red and Sudan Black series of dyes. Useful anthraquinone dyes include, but are not limited to: the Oil Blue dyes, and the Macrolex Blue series of dyes. Useful triphenylmethane dyes include, but are not limited to, Michler's hydrol, Malachite Green, Crystal Violet, and Auramine O.

C. Charge Control Agents and Particle Stabilizers

Charge control agents are used to provide good electrophoretic mobility to the electrophoretic particles. Stabilizers are used to prevent agglomeration of the electrophoretic particles, as well as prevent the electrophoretic particles from irreversibly depositing onto the capsule wall. Either component can be constructed from materials across a wide range of molecular weights (low molecular weight, oligomeric, or polymeric), and may be a single pure compound or a mixture. The charge control agent used to modify and/or stabilize the particle surface charge is applied as generally known in the arts of liquid toners, electrophoretic displays, non-aqueous paint dispersions, and engine-oil additives. In all of these arts, charging species may be added to non-aqueous media in order to increase electrophoretic mobility or increase electrostatic stabilization. The materials can improve steric stabilization as well. Different theories of charging are postulated, including selective ion adsorption, proton transfer, and contact electrification.

An optional charge control agent or charge director may be used. These constituents typically consist of low molecular weight surfactants, polymeric agents, or blends of one or more components and serve to stabilize or otherwise modify the sign and/or magnitude of the charge on the electrophoretic particles. The charging properties of the pigment itself may be accounted for by taking into account the acidic or basic surface properties of the pigment, or the charging sites may take place on the carrier resin surface (if present), or a combination of the two. Additional pigment properties which may be relevant are the particle size distribution, the chemical composition, and the lightfastness.

Charge adjuvants may also be added. These materials increase the effectiveness of the charge control agents or charge directors. The charge adjuvant may be a polyhydroxy compound or an aminoalcohol compound, and is preferably soluble in the suspending fluid in an amount of at least 2% by weight. Examples of polyhydroxy compounds which contain at least two hydroxyl groups include, but are not limited to, ethylene glycol, 2,4,7,9-tetramethyldecyn-4,7-diol, poly(propylene glycol), pentaethylene glycol, tripropylene glycol, triethylene glycol, glycerol, pentaerythritol, glycerol tris(12-hydroxystearate), propylene glycerol monohydroxystearate, and ethylene glycol monohydroxystearate. Examples of aminoalcohol compounds which contain at least one alcohol function and one amine function in the same molecule include, but are not limited to, triisopropanolamine, triethanolamine, ethanolamine, 3-amino-1-propanol, o-aminophenol, 5-amino-1-pentanol, and tetrakis(2-hydroxyethyl)ethylenediamine. The charge adjuvant is preferably present in the suspending fluid in an amount of about 1 to about 100 milligrams per gram ("mg/g") of the particle mass, and more preferably about 50 to about 200 mg/g.

The surface of the particle may also be chemically modified to aid dispersion, to improve surface charge, and to improve the stability of the dispersion, for example. Surface modifiers include organic siloxanes, organohalogen silanes and other functional silane coupling agents (Dow Coming® Z-6070, Z-6124, and 3 additive, Midland, Mich.); organic titanates and zirconates (Tyzor® TOT, TBT, and TE Series, du Pont); hydrophobing agents, such as long chain ($C_{12}$ to $C_{50}$) alkyl and alkyl benzene sulphonic acids, fatty amines or diamines and their salts or quaternary derivatives; and amphipathic polymers which can be covalently bonded to the particle surface.

In general, it is believed that charging results as an acid-base reaction between some moiety present in the continuous phase and the particle surface. Thus useful materials are those which are capable of participating in such a reaction, or any other charging reaction as known in the art.

Different non-limiting classes of charge control agents which are useful include organic sulfates or sulfonates, metal soaps, block or comb copolymers, organic amides, organic zwitterions, and organic phosphates and phosphonates. Useful organic sulfates and sulfonates include, but are not limited to, sodium bis(2-ethylhexyl) sulfosuccinate, calcium dodecylbenzenesulfonate, calcium petroleum sulfonate, neutral or basic barium dinonylnaphthalene sulfonate, neutral or basic calcium dinonylnaphthalene sulfonate, dodecylbenzenesulfonic acid sodium salt, and ammonium lauryl sulfate. Useful metal soaps include, but are not limited to, basic or neutral barium petronate, calcium petronate, Co-, Ca-, Cu-, Mn-, Ni-, Zn-, and Fe-salts of naphthenic acid, Ba-, Al-, Zn-, Cu-, Pb-, and Fe-salts of stearic acid, divalent and trivalent metal carboxylates, such as aluminum tristearate, aluminum octanoate, lithium heptanoate, iron stearate, iron distearate, barium stearate, chromium stearate, magnesium octanoate, calcium stearate, iron naphthenate, zinc naphthenate, Mn- and Zn-heptanoate, and Ba-, Al-, Co-, Mn-, and Zn-octanoate. Useful block or comb copolymers include, but are not limited to, AB diblock copolymers of (A) polymers of 2-(N,N-dimethylamino) ethyl methacrylate quaternized with methyl p-toluenesulfonate and (B) poly(2-ethylhexyl methacrylate), and comb graft copolymers with oil soluble tails of poly (12-hydroxystearic acid) and having a molecular weight of about 1800, pendant on an oil-soluble anchor group of poly(methyl methacrylate-methacrylic acid). Useful organic amides include, but are not limited to, polyisobutylene and similar succinimides such as OLOA 371 and 1200 (available from Chevron Corporation, 575 Market Street, San Francisco Calif. 94105), and N-vinylpyrrolidone polymers. Useful organic zwitterions include, but are not limited to, lecithin. Useful organic phosphates and phosphonates include, but are not limited to, the sodium salts of phosphated mono- and di-glycerides with saturated and unsaturated acid substituents.

Particle dispersion stabilizers may be added to prevent particle flocculation or attachment to the capsule walls. For the typical high resistivity liquids used as suspending fluids in electrophoretic displays, non-aqueous surfactants may be used. These include, but are not limited to, glycol ethers, acetylenic glycols, alkanolamides, sorbitol derivatives, alkyl amines, quaternary amines, imidazolines, dialkyl oxides, and sulfosuccinates.

D. Encapsulation

Encapsulation of the internal phase may be accomplished in a number of different ways. Numerous suitable procedures for microencapsulation are detailed in both Microencapsulation, Processes and Applications, (I. E. Vandegaer, ed.), Plenum Press, New York, N.Y. (1974) and Gutcho, Microcapsules and Microencapsulation Techniques, Noyes Data Corp., Park Ridge, N.J. (1976). The processes fall into several general categories, all of which can be applied to the present invention: interfacial polymerization, in situ polymerization, physical processes, such as coextrusion and other phase separation processes, in-liquid curing, and simple/complex coacervation.

Numerous materials and processes should prove useful in formulating displays of the present invention. Useful materials for simple coacervation processes to form the capsule include, but are not limited to, gelatin, poly(vinyl alcohol), poly(vinyl acetate), and cellulosic derivatives, such as, for example, carboxymethylcellulose. Useful materials for complex coacervation processes include, but are not limited to, gelatin, acacia, carageenan, carboxymethylcellulose, hydrolyzed styrene anhydride copolymers, agar, alginate, casein, albumin, methyl vinyl ether co-maleic anhydride, and cellulose phthalate. Useful materials for phase separation processes include, but are not limited to, polystyrene, poly(methyl methacrylate) (PMMA), poly(ethyl methacrylate), poly(butyl methacrylate), ethyl cellulose, poly(vinylpyridine), and polyacrylonitrile. Useful materials for in situ polymerization processes include, but are not limited to, polyhydroxyamides, with aldehydes, melamine, or urea and formaldehyde; water-soluble oligomers of the condensate of melamine, or urea and formaldehyde; and vinyl monomers, such as, for example, styrene, methyl methacrylate (MMA) and acrylonitrile. Finally, useful materials for interfacial polymerization processes include, but are not limited to, diacyl chlorides, such as, for example, sebacoyl, adipoyl, and di- or poly-amines or alcohols, and isocyanates. Useful emulsion polymerization materials may include, but are not limited to, styrene, vinyl acetate, acrylic acid, butyl acrylate, t-butyl acrylate, methyl methacrylate, and butyl methacrylate.

Capsules produced may be dispersed into a curable carrier, resulting in an ink which may be printed or coated on large and arbitrarily shaped or curved surfaces using conventional printing and coating techniques.

In the context of the present invention, one skilled in the art will select an encapsulation procedure and wall material based on the desired capsule properties. These properties include the distribution of capsule radii; electrical, mechanical, diffusion, and optical properties of the capsule wall; and chemical compatibility with the internal phase of the capsule.

The capsule wall generally has a high electrical resistivity. Although it is possible to use walls with relatively low resistivities, this may limit performance in requiring relatively higher addressing voltages. The capsule wall should also be mechanically strong (although if the finished capsule powder is to be dispersed in a curable polymeric binder for coating, mechanical strength is not as critical). The capsule wall should generally not be porous. If, however, it is desired to use an encapsulation procedure that produces porous capsules, these can be overcoated in a post-processing step (i.e., a second encapsulation). Moreover, if the capsules are to be dispersed in a curable binder, the binder will serve to close the pores. The capsule walls should be optically clear. The wall material may, however, be chosen to match the refractive index of the internal phase of the capsule (i.e., the suspending fluid) or a binder in which the capsules are to be dispersed. For some applications (e.g., interposition between two fixed electrodes), monodispersed capsule radii are desirable.

An encapsulation technique that is suited to the present invention involves a polymerization between urea and formaldehyde in an aqueous phase of an oil/water emulsion in the presence of a negatively charged, carboxyl-substituted, linear hydrocarbon polyelectrolyte material. The resulting capsule wall is a urea/formaldehyde copolymer, which discretely encloses the internal phase. The capsule is clear, mechanically strong, and has good resistivity properties.

The related technique of in situ polymerization utilizes an oil/water emulsion, which is formed by dispersing the electrophoretic fluid (i.e., the dielectric liquid containing a suspension of the pigment particles) in an aqueous environment. The monomers polymerize to form a polymer with higher affinity for the internal phase than for the aqueous phase, thus condensing around the emulsified oily droplets. In one in situ polymerization process, urea and formaldehyde condense in the presence of poly(acrylic acid) (see, e.g., U.S. Pat. No. 4,001,140). In other processes, described in U.S. Pat. No. 4,273,672, any of a variety of cross-linking agents borne in aqueous solution is deposited around microscopic oil droplets. Such cross-linking agents include aldehydes, especially formaldehyde, glyoxal, or glutaraldehyde; alum; zirconium salts; and polyisocyanates.

The coacervation approach also utilizes an oil/water emulsion. One or more colloids are coacervated (i.e., agglomerated) out of the aqueous phase and deposited as shells around the oily droplets through control of temperature, pH and/or relative concentrations, thereby creating the microcapsule. Materials suitable for coacervation include gelatins and gum arabic. See, e.g., U.S. Pat. No. 2,800,457.

The interfacial polymerization approach relies on the presence of an oil-soluble monomer in the electrophoretic composition, which once again is present as an emulsion in an aqueous phase. The monomers in the minute hydrophobic droplets react with a monomer introduced into the aqueous phase, polymerizing at the interface between the droplets and the surrounding aqueous medium and forming shells around the droplets. Although the resulting walls are relatively thin and may be permeable, this process does not require the elevated temperatures characteristic of some other processes, and therefore affords greater flexibility in terms of choosing the dielectric liquid.

Coating aids can be used to improve the uniformity and quality of the coated or printed electrophoretic ink material. Wetting agents are typically added to adjust the interfacial tension at the coating/substrate interface and to adjust the liquid/air surface tension. Wetting agents include, but are not limited to, anionic and cationic surfactants, and nonionic species, such as silicone or fluoropolymer-based materials. Dispersing agents may be used to modify the interfacial tension between the capsules and binder, providing control over flocculation and particle settling.

Surface tension modifiers can be added to adjust the air/ink interfacial tension. Polysiloxanes are typically used in such an application to improve surface leveling while minimizing other defects within the coating. Surface tension modifiers include, but are not limited to, fluorinated surfactants, such as, for example, the Zonyl® series from du Pont, the Fluorad® series from Minnesota Mining and Manufacturing Corporation (St. Paul, Minn.), and the fluoroalkyl series from Autochem (Glen Rock, N.J.); siloxanes, such as, for example, Silwet® from Union Carbide (Danbury, Conn.); and polyethoxy and polypropoxy alcohols. Antifoams, such as silicone and silicone-free polymeric materials, may be added to enhance the movement of air from within the ink to the surface and to facilitate the rupture of bubbles at the coating surface. Other useful antifoams include, but are not limited to, glyceryl esters, polyhydric alcohols, compounded antifoams, such as oil solutions of alkylbenzenes, natural fats, fatty acids, and metallic soaps, and silicone antifoaming agents made from the combination of dimethyl siloxane polymers and silica. Stabilizers such as UV-absorbers and antioxidants may also be added to improve the lifetime of the ink.

E. Binder Material

The binder typically is used as an adhesive medium that supports and protects the capsules, as well as binds the electrode materials to the capsule dispersion. A binder can be non-conducting, semiconductive, or conductive. Binders are available in many forms and chemical types. Among these are water-soluble polymers, water-borne polymers, oil-soluble polymers, thermoset and thermoplastic polymers, and radiation-cured polymers.

Among the water-soluble polymers are the various polysaccharides, the polyvinyl alcohols, N-methylpyrrolidone, N-vinylpyrrolidone, the various Carbowax® species (Union Carbide, Danbury, Conn.), and poly(2-hydroxyethyl acrylate).

The water-dispersed or water-borne systems are generally latex compositions, typified by the Neorez® and Neocryl® resins (Zeneca Resins, Wilmington, Mass.), Acrysol® (Rohm and Haas, Philadelphia, Pa.), Bayhydrol® (Bayer, Pittsburgh, Pa.), and the Cytec Industries (West Paterson, N.J.) HP line. These are generally latices of polyurethanes, occasionally compounded with one or more of the acrylics, polyesters, polycarbonates or silicones, each lending the final cured resin in a specific set of properties defined by glass transition temperature, degree of "tack," softness, clarity, flexibility, water permeability and solvent resistance, elongation modulus and tensile strength, thermoplastic flow, and solids level. Some water-borne systems can be mixed with reactive monomers and catalyzed to form more complex resins. Some can be further cross-linked by the use of a cross-linking reagent, such as an aziridine, for example, which reacts with carboxyl groups.

A typical application of a water-borne resin and aqueous capsules follows. A volume of particles is centrifuged at low speed to separate excess water. After a given centrifugation process, for example 10 minutes at 60× gravity ("g"), the capsules are found at the bottom of the centrifuge tube, while the water portion is at the top. The water portion is carefully removed (by decanting or pipetting). The mass of the remaining capsules is measured, and a mass of resin is added such that the mass of resin is, for example, between one eighth and one tenth of the weight of the capsules. This mixture is gently mixed on an oscillating mixer for approximately one half hour. After about one half hour, the mixture is ready to be coated onto the appropriate substrate.

The thermoset systems are exemplified by the family of epoxies. These binary systems can vary greatly in viscosity, and the reactivity of the pair determines the "pot life" of the mixture. If the pot life is long enough to allow a coating operation, capsules may be coated in an ordered arrangement in a coating process prior to the resin curing and hardening.

Thermoplastic polymers, which are often polyesters, are molten at high temperatures. A typical application of this type of product is hot-melt glue. A dispersion of heat-resistant capsules could be coated in such a medium. The solidification process begins during cooling, and the final hardness, clarity and flexibility are affected by the branching and molecular weight of the polymer.

Oil or solvent-soluble polymers are often similar in composition to the water-borne system, with the obvious exception of the water itself. The latitude in formulation for solvent systems is enormous, limited only by solvent choices and polymer solubility. Of considerable concern in solvent-based systems is the viability of the capsule itself, the integrity of the capsule wall cannot be compromised in any way by the solvent.

Radiation cure resins are generally found among the solvent-based systems. Capsules may be dispersed in such a medium and coated, and the resin may then be cured by a timed exposure to a threshold level of ultraviolet radiation, either long or short wavelength. As in all cases of curing polymer resins, final properties are determined by the branching and molecular weights of the monomers, oligomers and cross-linkers.

A number of "water-reducible" monomers and oligomers are, however, marketed. In the strictest sense, they are not water soluble, but water is an acceptable diluent at low concentrations and can be dispersed relatively easily in the mixture. Under these circumstances, water is used to reduce the viscosity (initially from thousands to hundreds of thousands centipoise). Water-based capsules, such as those made from a protein or polysaccharide material, for example, could be dispersed in such a medium and coated, provided the viscosity could be sufficiently lowered. Curing in such systems is generally by ultraviolet radiation.

Like other encapsulated electrophoretic displays, the encapsulated electrophoretic displays of the present invention provide flexible, reflective displays that can be manufactured easily and consume little power (or no power in the case of bistable displays in certain states). Such displays, therefore, can be incorporated into a variety of applications and can take on many forms. Once the electric field is removed, the electrophoretic particles can be generally stable. Additionally, providing a subsequent electric charge can alter a prior configuration of particles. Such displays may include, for example, a plurality of anisotropic particles and a plurality of second particles in a suspending fluid. Application of a first electric field may cause the anisotropic particles to assume a specific orientation and present an optical property. Application of a second electric field may then cause the plurality of second particles to translate, thereby disorienting the anisotropic particles and disturbing the optical property. Alternatively, the orientation of the anisotropic particles may allow easier translation of the plurality of second particles. Alternatively or in addition, the particles may have a refractive index that substantially matches the refractive index of the suspending fluid.

As already mentioned, an encapsulated electrophoretic display can be constructed so that the optical state of the display is stable for some length of time. When the display has two states that are stable in this manner, the display is bistable, within the meaning of that term as previously defined; if more than two states of the display are stable, then the display is multistable. However, whether a display is effectively bistable state depends upon the display's application. A slowly decaying optical state can be effectively bistable if the optical state is substantially unchanged over the required viewing time. For example, in a display that is updated every few minutes, a display image that is stable for hours or days is effectively bistable for a particular application. Alternatively, it is possible to construct encapsulated electrophoretic displays in which the image decays quickly once the addressing voltage to the display is removed (i.e., the display is not bistable or multistable). Whether or not an encapsulated electrophoretic display is bistable, and its degree of bistability, can be controlled through appropriate chemical modification of the electrophoretic particles, the suspending fluid, the capsule, and binder materials.

An encapsulated electrophoretic display may take many forms. The capsules of such a display may be of any size or shape. The capsules may, for example, be spherical and may have diameters in the millimeter range or the micron range, but are preferably from about ten to about a few hundred microns. The particles within the capsules of such a display may be colored, luminescent, light-absorbing or transparent, for example.

The following Examples are now given. though by way of illustration only, to show details of preferred reagents, conditions and techniques used in the electrophoretic media and displays of the present invention, and the advantages achieved by the use of free radical scavengers in accordance with the present invention.

Experimental Procedure

Except as otherwise noted, the encapsulated electrophoretic displays used in the Examples below were produced and tested by the following procedure.

(i) Preparation of Internal Phase

A dye solution was prepared by placing ISOPAR G (2000 g, available from Chevron Corporation) and Halocarbon 1.8 (2000 g, available from Halogenated Hydrocarbon Inc., River Edge N.J.) in a 4 L flask, then adding a blue dye (approximately 19 g of Bayer Blue—3R, available from Bayer Corporation, 100 Bayer Rd., Pittsburgh Pa. 15205-9741) and stirring the resultant mixture at 45±5° C. for 6–12 hours until the dye had completely dissolved, then allowing the solution to cool to room temperature.

To a 2000 g portion of the cooled solution were added successively OLOA 371 (22.3 g. of a 20% w/w solution; this material acts as a charge control agent), Span 85 (8.4 g; this material is a surfactant available from Sigma-Aldrich, Inc.) and titania (100.5 g of R104 titania, available from du Pont). The resultant mixture was shaken manually, sonicated for 10 minutes at power 9 in an Aquasonic Model 75D sonicator (VWR Scientific Products, 1310 Goshen Parkway, West Chester, Pa. 19380), re-shaken manually, sonicated for an additional 10 minutes, again shaken manually and placed in storage.

12 To 24 hours before this stored mixture was to be used to form capsules by the procedure described in Section (ii) below, the mixture was shaken manually to redisperse the titania and the free radical scavenger (if any) was added.

(ii) Preparation of Capsules

Cold water (2622 g) was added to a 4 L glass reactor equipped with a heating/cooling jacket and a mechanical stirrer, and gelatin (45 g) was added slowly over a period of about 30 seconds, without stirring. The resultant mixture was allowed to stand for 1 hour without stirring to allow the gelatin to swell, then stirred gently for 30 minutes to allow the gelatin to dissolve. During this stirring, warm water was passed through the jacket so that at the end of the 30 minute period the temperature of the gelatin solution was 40° C. Separately, the internal phase (1000 g) prepared in Section (i) above was sonicated for 10 minutes in the same manner as previously described, and then flowed into the gelatin solution slowly over a 15 minute period through a dropping funnel having its outlet positioned below the surface of this solution, while the solution was stirred vigorously. After the addition was complete, the resultant mixture was stirred vigorously for a further 30 minutes, and then an acacia solution (33.3 g of acacia in 655 g of water at a temperature of 40° C.) was added over a period of 1 minute, the stirring speed being reduced to prevent foam formation during this addition. The pH of the resultant mixture was reduced to 4.7 with 10% aqueous acetic acid and the stirring was continued for a further 40 minutes. The temperature of the resultant mixture was then reduced to 10° C. over a period of 2 hours, and at this temperature glutaraldehyde (16.7 g) was added with continued stirring. Finally, the mixture was stirred gently for 12 hours, with its temperature being gradually raised to 25° C. during the first part of this period, and the contents of the reactor were then removed, the capsules (which has a average diameter of about 300 μm) separated from the liquid phase and washed (by redispersion and sedimentation) with water until the pH of the wash water was 5.0.

(iii) Production of Electrophoretic Display

The capsule slurry produced in Section (ii) above was mixed with an aqueous urethane binder (NeoRez R-9320 from Zeneca Resins, Wilmington Mass.) at a weight ratio of one part binder to 10 parts capsules. If a coating additive (see Examples below) was to be used, it was also added at this time. The resultant mixture was then coated either by hand coating or by means of a slot coater on to indium-tin oxide sputtered polyester film; the thickness of the indium-tin oxide layer was approximately 100–125 μm. The amount of the capsule mixture applied to the film was controlled so as to lay down (as far as possible) a single layer of capsules; cf. copending and commonly assigned application Ser. No. 09/413,444, filed Oct. 6, 1999 and the corresponding and the corresponding International Application PCT/US99/23313 (Publication No. WO 00/20922)—the entire disclosures of these applications are herein incorporated by reference. The coated film was then dried in hot air (60° C.) for 30 minutes, and then hot laminated at 60° C. using an anisotropic tape to a backplane comprising an approximately 100–25 μm thick sheet of polyester screen printed with thick film silver and dielectric inks; this lamination was conducted at a pressure of 15 psig in a hot roll laminator from Cheminstruments, Fairfield Ohio.

(iv) Testing Procedure

Sample displays prepared as described in Section (iii) above were driven using 90 Volt square wave pulses of 500 millisecond duration, the displays being switched constantly at a cycle time of 1.0 seconds. The displays were exposed to continuous indoor fluorescent lighting of approximately 1000 lux and ambient temperature (approximately 21° C.) and humidity. At intervals the reflectivities of the blue and white optical states of each display were measured using a SpectraScan (Registered Trade Mark) PR-650 spectroradiometer (available from Photo Research, Inc., 9732 Topanga Canyon Place, Chatsworth Calif. 91311-4135).

EXAMPLE 1

This Example illustrates the improvement in working lifetime in hand-coated displays achieved using the preferred TEMPO stable free radical.

Electrophoretic displays were prepared as described above using (A) no free radical scavenger; (B) 0.1 weight percent of the aforementioned TEMPO stable free radical; and (C) an equimolar amount ($6.4 \times 10^{-3}$ molar) of Tinuvin 292, a conventional hindered amine free radical scavenger. The displays were hand-coated, and the results obtained are shown in Table 1 below, while the reflectivities of the white states as a function of time are plotted in FIG. 1 of the accompanying drawings.

TABLE 1

| | Scavenger | Time (hrs) | | | | |
|---|---|---|---|---|---|---|
| | | 0 | 168 | 1365 | 2176 | 2831 |
| | | Reflectivity, % | | | | |
| White State | None | 26.3 | 26.8 | 16.2 | 10.9 | 9.4 |
| | TEMPO | 26.9 | 26.6 | 27.1 | 21.8 | 20.0 |
| | T292 | 26.0 | 26.6 | 25.3 | 9.3 | 4.0 |
| Dark State | None | 1.4 | 1.5 | 2.2 | 2.3 | 2.5 |
| | TEMPO | 1.5 | 1.7 | 2.7 | 2.5 | 2.5 |
| | T292 | 1.5 | 1.4 | 2.1 | 2.3 | 1.8 |

In Table 1 and FIG. 1, the working lifetime of the display may reasonably be estimated as the time at which the reflectivity of the white state falls to about 20%. On this basis, the working lifetime of the display without any free radical scavenger may be estimated at about 900–1000 hours, that of the display containing Tinuvin 292 at about 1700–1800 hours (although note that, at long operating times, the performance of this display is actually worse than that of the display with no scavenger), and the lifetime of the display containing TEMPO at more than 2800 hours.

EXAMPLE 2

This Example illustrates the improvement in working lifetime in both hand-coated and machine-coated displays achieved using the preferred TEMPO stable free radical.

Electrophoretic displays were prepared as described above using (A) no free radical scavenger; and (B) 0.1 weight percent of the aforementioned TEMPO stable free radical. Two separate batches of material containing no free radical scavenger were prepared and formed into displays. Each of the materials was coated both by hand and by a slot coater; in all the machine-coated displays, 0.2 percent by weight of the slurry of hydroxypropyl-methylcellulose, molecular weight approximately 90,000 (available from Sigma-Aldrich, Inc.) was added as a coating additive to increase the viscosity of the slurry. The results obtained are shown in Table 2 below, while the reflectivities of the white states as a function of time are plotted in FIG. 2 of the accompanying drawings. In Table 2, "(H)" in the "Scavenger" column indicates hand-coating and "(M)" in the same column indicates machine-coating. Only the TEMPO-containing displays were measured at 2785 hours of operation because the other displays had clearly failed after 1785 hours.

TABLE 2

| | Scavenger | Time (hrs) | | | | | |
|---|---|---|---|---|---|---|---|
| | | 0 | 337 | 1006 | 1286 | 1785 | 2785 |
| | | Reflectivity, % | | | | | |
| White State | None (H) | 28.0 | 29.1 | 25.8 | 24.2 | 14.9 | — |
| | None (H) | 29.7 | 30.1 | 27.2 | 25.0 | 15.2 | — |
| | None (M) | 29.2 | 28.2 | 25.2 | 21.8 | 9.2 | — |
| | None (M) | 29.8 | 30.9 | 23.4 | 17.9 | 7.9 | — |
| | TEMPO (H) | 29.2 | 27.8 | 26.1 | 26.8 | 27.7 | 26.4 |
| | TEMPO (M) | 30.5 | 29.1 | 29.0 | 29.1 | 28.6 | 26.3 |
| Dark State | None (H) | 1.8 | 2.3 | 1.9 | 2.3 | 2.2 | — |
| | None (H) | 3.2 | 3.4 | 1.9 | 2.3 | 2.2 | — |
| | None (M) | 1.8 | 2.3 | 2.1 | 2.4 | 3.1 | — |
| | None (M) | 2.4 | 3.0 | 2.1 | 2.4 | 2.3 | — |
| | TEMPO (H) | 1.8 | 2.9 | 2.9 | 2.5 | 3.6 | 4.1 |
| | TEMPO (M) | 2.0 | 2.7 | 2.3 | 2.1 | 3.6 | 4.2 |

Figure 2:
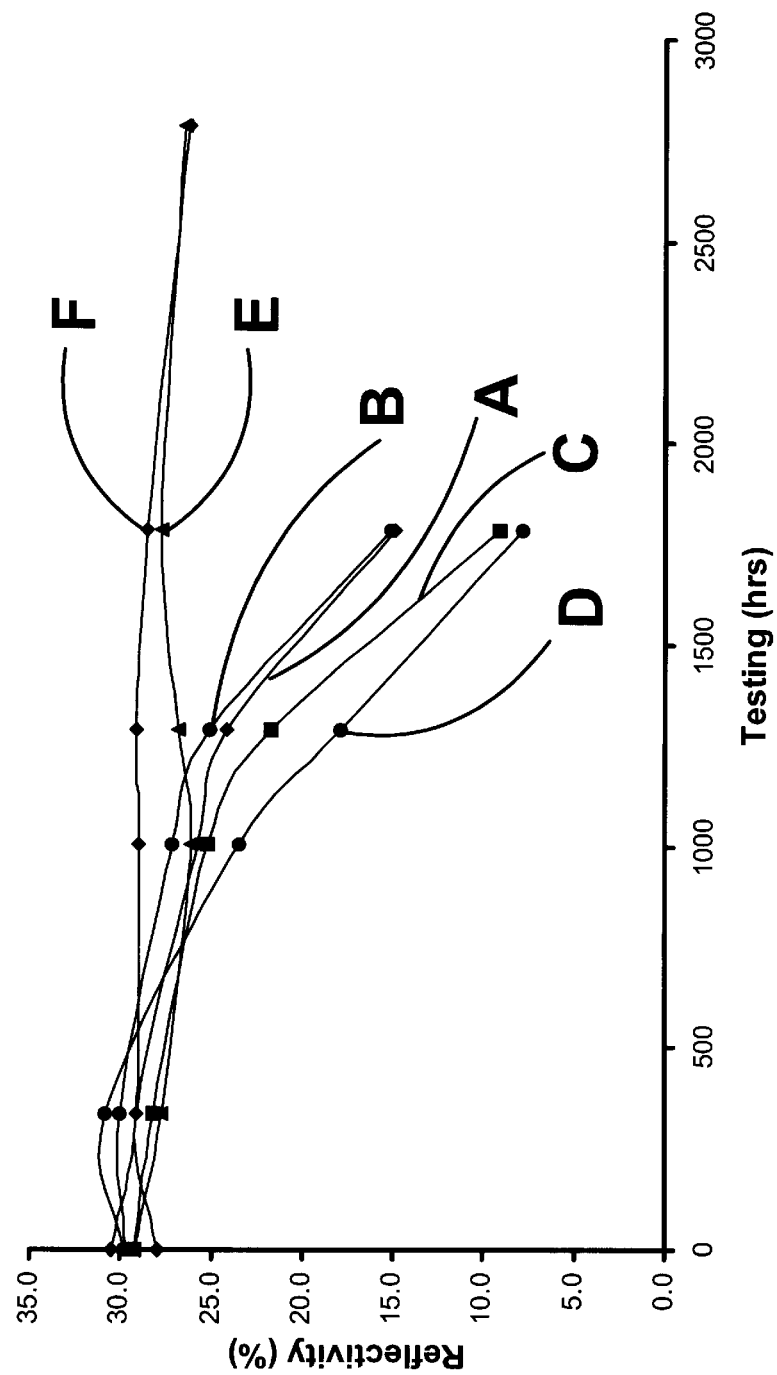

In Table 2 and FIG. 2, the working lifetime of the display may reasonably be estimated as the time at which the reflectivity of the white state falls to about 20%. On this basis, the working lifetimes of all the displays without any free radical scavenger, whether hand-coated (Curves A and B in FIG. 2) or machine-coated (Curves C and D in FIG. 2) may be estimated at about 1200–1600 hours, with the lifetime of the machine-coated displays being slightly less than that of the hand-coated displays. In contrast, the lifetimes of the displays containing TEMPO, whether hand-coated or machine-coated (Curves E and F respectively in FIG. 2) may be estimated at substantially greater than 3000 hours.

EXAMPLE 3

This Example illustrates the improvement in working lifetime in both hand-coated and machine-coated displays achieved using the preferred TEMPO stable free radical.

Example 2 was repeated, except that one hand-coated display and one machine-coated display were prepared without free radical scavenger, and that 0.2 percent by weight of the slurry of Drewthix (a commercial coating additive, available from Ashland Inc., 1000 Ashland Drive, Russell Ky. 41169) was used instead of hydroxypropylmethylcellulose as the coating additive in the machine-coated displays.

The results obtained are shown in Table 3 below, while the reflectivities of the white states as a function of time are plotted in FIG. 3 of the accompanying drawings. In Table 3, "(H)" in the "Scavenger" column indicates hand-coating and "(M)" in the same column indicates machine-coating. Only the TEMPO-containing displays were measured at 2785 hours of operation because the other displays had clearly failed after 1785 hours.

TABLE 3

| | Scavenger | Time (hrs) | | | | | |
|---|---|---|---|---|---|---|---|
| | | 0 | 337 | 1006 | 1286 | 1785 | 2785 |
| | | Reflectivity, % | | | | | |
| White State | None (H) | 28.0 | 29.1 | 25.8 | 24.2 | 14.9 | — |
| | None (M) | 25.7 | 27.7 | 23.4 | 15.0 | 4.7 | — |
| | TEMPO (H) | 29.2 | 27.8 | 26.1 | 26.8 | 27.7 | 26.4 |
| | TEMPO (M) | 30.3 | 29.9 | 29.6 | 28.3 | 27.4 | 26.3 |
| Dark State | None (H) | 1.8 | 2.3 | 1.9 | 2.3 | 2.2 | — |
| | None (M) | 2.0 | 2.5 | 2.4 | 2.6 | 2.4 | — |
| | TEMPO (H) | 1.8 | 2.9 | 2.9 | 2.5 | 3.6 | 4.1 |
| | TEMPO (M) | 2.1 | 3.4 | 2.3 | 2.2 | 3.7 | 4.8 |

Figure 3:
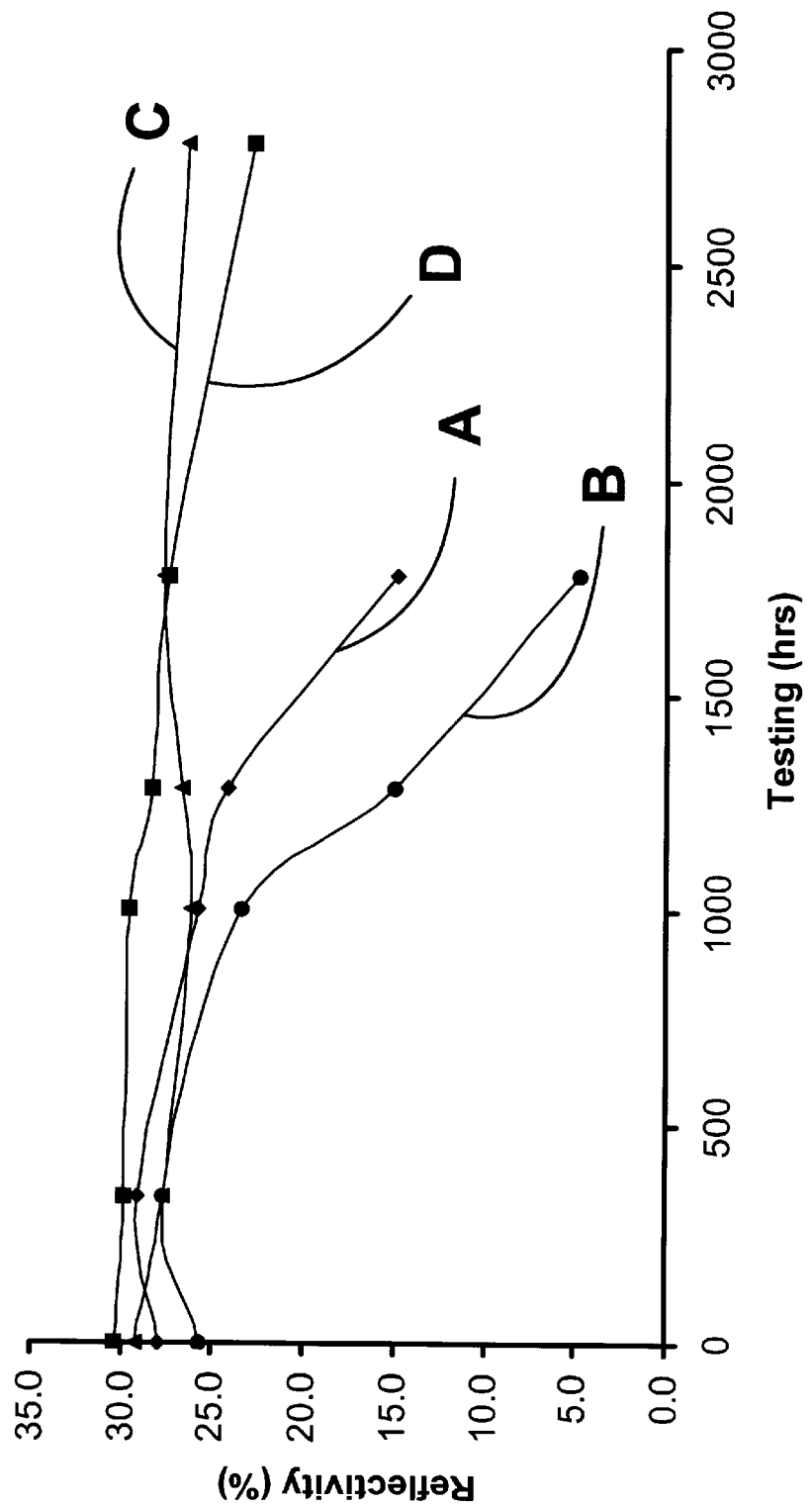

In Table 3 and FIG. 3, the working lifetime of the display may reasonably be estimated as the time at which the reflectivity of the white state falls to about 20%. On this basis, the working lifetimes of all the displays without any free radical scavenger, whether hand-coated (Curve A in FIG. 3) or machine-coated (Curve B in FIG. 3) may be estimated at about 1200–1600 hours, with the lifetime of the machine-coated display being slightly less than that of the hand-coated display. In contrast, the lifetimes of the displays containing TEMPO, whether hand-coated or machine-coated (Curves C and D respectively in FIG. 3) may be estimated at well in excess of 2500 hours.

From the foregoing description, it will be seen that the electrophoretic media and displays of the present invention preserve all the advantages of prior art encapsulated electrophoretic media and displays, while rendering the encapsulated electrophoretic medium less susceptible to degradation, especially photoinduced degradation, during use. Thus, the media and displays of the present invention have longer working lifetimes than similar prior art media and displays, and may be useful in applications where prior art encapsulated electrophoretic media and displays cannot be used because of their susceptibility to photoinduced and other degradation.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. An electrophoretic medium comprising a liquid and at least one particle disposed within the liquid and capable of moving therethrough on application of an electric field to the medium, the medium further comprising a free radical scavenger selected from the group consisting of (a) stable free radicals; and (b) polymeric free radical scavengers comprising a plurality of free radical scavenging groups attached to a polymeric chain.

2. An electrophoretic medium according to claim 1 wherein the free radical scavenger is a stable free radical.

3. An electrophoretic medium according to claim 2 wherein the stable free radical is derived from an amine oxide.

4. An electrophoretic medium according to claim 3 wherein the stable free radical is derived from a piperidine oxide.

5. An electrophoretic medium according to claim 4 wherein the stable free radical is derived from a 2,2,6,6-tetraalkylpiperidine oxide.

6. An electrophoretic medium according to claim 5 wherein the stable free radical comprises 2,2,6,6-tetramethylpiperidyloxy.

7. An electrophoretic medium according to claim 1 wherein the free radical scavenger is a polymeric free radical scavenger.

8. An electrophoretic medium according to claim 7 wherein the free radical scavenging groups in the polymeric free radical scavenger comprise nitrogenous heterocyclic groups.

9. An electrophoretic medium according to claim 8 wherein the free radical scavenging groups in the polymeric free radical scavenger comprise piperidine groups.

10. An electrophoretic medium according to claim 9 wherein the free radical scavenging groups in the polymeric free radical scavenger comprise 2,2,6,6-substituted piperidine groups bearing a hydrocarbon or hydrocarbonoxy group on the nitrogen atom.

11. An electrophoretic medium according to claim 1 wherein the free radical scavenger comprises from about 0.01 to about 1 percent by weight of the medium.

12. An electrophoretic medium according to claim 11 wherein the free radical scavenger comprises from about 0.05 to about 0.2 percent by weight of the medium.

13. An electrophoretic medium according to claim 1 further comprising an ultra-violet absorber and/or quencher.

14. An electrophoretic medium according to claim 13 wherein the ultra-violet absorber and/or quencher is selected from the group consisting of triazine derivatives, benzoxazinones, hydroxy-substituted benzophenones, hydroxy-substituted benzotriazoles, nickel complexes, formamidines and oxamide derivatives.

15. An electrophoretic medium according to claim 13 wherein the ultra-violet absorber and/or quencher comprises from about 0.02 to about 5 percent by weight of the medium.

16. An electrophoretic medium according to claim 15 wherein the ultra-violet absorber and/or quencher comprises from about 0.2 to about 2 percent by weight of the medium.

17. An electrophoretic medium according to claim 1 which is encapsulated, the medium comprising a plurality of capsules each of which comprises a capsule wall enclosing the liquid and the at least one particle.

18. An electrophoretic medium according to claim 17 further comprising a binder disposed between the capsules and binding the capsules to one another.

19. An electrophoretic medium according to claim 1 wherein the liquid has an optical property differing from that of the at least one particle.

20. An electrophoretic medium according to claim 1 wherein the liquid has disposed therein at least one first particle having a first optical property and a first electrophoretic mobility and at least one second particle having a second optical property different from the first optical property and a second electrophoretic mobility different from the first electrophoretic mobility.

21. A medium according to claim 20 wherein the first and second particles bear charges of opposite polarity.

22. An electrophoretic display comprising an electrophoretic medium according to claim 1 in combination with first and second electrodes disposed on opposed sides of the electrophoretic medium, at least one of the first and second electrodes being light transmissive.

23. An electrophoretic display according to claim 22 further comprising first and second substrates disposed on opposed sides of the electrophoretic medium, the first and second substrates being secured to the first and second electrodes respectively.

* * * * *